United States Patent
Rabinovitz et al.

(10) Patent No.: US 7,628,753 B2
(45) Date of Patent: Dec. 8, 2009

(54) METHOD FOR IN VIVO SENSING (75) Inventors: Raphael Rabinovitz, Raanana (IL); Danny Afik, Misgav (IL); Daniel Gat, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 273 days.

(21) Appl. No.: 11/452,404

(22) Filed: Jun. 14, 2006

(65) Prior Publication Data

US 2006/0235275 A1 Oct. 19, 2006

Related U.S. Application Data (63) Continuation-in-part of application No. 10/541,191, filed as application No. PCT/IL03/01117 on Dec. 30, 2003.

(60) Provisional application No. 60/436,651, filed on Dec. 30, 2002.

(51) Int. Cl.
  *A61B 1/06* (2006.01)
  *A61B 1/04* (2006.01)
  *A61B 6/00* (2006.01)

(52) U.S. Cl. .................. 600/160; 600/112; 600/476

(58) Field of Classification Search .............. 600/112, 600/143, 183, 300, 302, 407; 128/898
See application file for complete search history.

(56) References Cited

U.S. PATENT DOCUMENTS

| 4,278,077 A | 7/1981 | Mizumoto |
| 5,122,362 A * | 6/1992 | Phillips et al. ............. 435/14 |
| 5,437,880 A * | 8/1995 | Takaichi et al. ............ 426/73 |
| 5,604,531 A | 2/1997 | Iddan et al. |
| 5,853,757 A | 12/1998 | Durand et al. |
| 5,980,462 A * | 11/1999 | Maruta ...................... 600/462 |
| 5,993,378 A | 11/1999 | Lemelson |
| 6,240,312 B1 | 5/2001 | Alfano et al. |
| 6,257,238 B1 * | 7/2001 | Meah ......................... 128/859 |
| 6,319,195 B1 * | 11/2001 | Nakaichi et al. ............ 600/120 |
| 6,324,418 B1 | 11/2001 | Crowley et al. |
| 7,039,453 B2 * | 5/2006 | Mullick et al. ............ 600/476 |
| 7,083,579 B2 * | 8/2006 | Yokoi et al. ............... 600/593 |
| 2002/0103417 A1 | 8/2002 | Gazdzinski |
| 2003/0020810 A1 * | 1/2003 | Takizawa et al. ............ 348/68 |
| 2003/0191430 A1 | 10/2003 | D'Andrea et al. |
| 2004/0082850 A1 * | 4/2004 | Bonner et al. ............. 600/424 |
| 2007/0260175 A1 * | 11/2007 | Segawa et al. .............. 604/79 |

OTHER PUBLICATIONS

International Search Report for International Publication No. PCT/IL03/01117 mailed on Oct. 4, 2004.

\* cited by examiner

*Primary Examiner*—Eric F Winakur
*Assistant Examiner*—Michael T Rozanski
(74) *Attorney, Agent, or Firm*—Pearl Cohen Zedek Latzer, LLP (57) ABSTRACT

A method for in vivo sensing of a body lumen such as a lumen in the upper GI tract is provided. The method may include, for example, inserting a sensing device into a subject's body lumen, positioning the subject in a horizontal or other suitable position, and receiving data transmitted from the sensing device.

8 Claims, 3 Drawing Sheets

METHOD FOR IN VIVO SENSING

CROSS-REFERENCE TO RELATED APPLICATION

This application is a continuation-in-part of U.S. application Ser. No. 10/541,191, filed Feb. 15, 2007, which is a National Phase Application of PCT International Application No. PCT/IL03/01117, International Filing Date Dec. 30, 2003, which claims priority of U.S. Patent application, 60/436,651, filed Dec. 30, 2002 all of which are hereby incorporated by reference in their entirety.

FIELD OF THE INVENTION

The present invention relates to the field of in vivo diagnostics. More specifically, the present invention relates to a method for sensing, for example, imaging, a body lumen.

BACKGROUND OF THE INVENTION

Dyspeptic symptoms (dyspepsia) constitute a major reason for physician visits and referral for gastroenterology consultation. Some pathologies of the gastrointestinal (GI) tract, involve epithelial damage, erosions, and ulcers. For example, inflammation of the GI tract mucosa (typically in the stomach), such as gastritis, can be characterized, inter alia, based on the endoscopic appearance of the gastric mucosa (e.g., varioliform gastritis). Other pathologies may involve irregularities or abnormal appearances of folds, polyps or color indications (such as bleeding) on the GI tract wall. Detection of these pathologies at an initial stage plays an important role in enhancing the probability of a cure.

Screening populations for initial signs of GI tract pathologies is typically carried out by non invasive methods including x-ray series in which a patient intakes x-ray opaque (radio-opaque) material (barium, gastrographine, or others). The material resides for some time on the walls of the GI tract, enabling examination of the x-ray images of the GI tract. This technique has several drawbacks, namely, low detection rate and exposure to x-ray radiation. Other screening methods include viewing the GI tract walls or lumens by means of appropriate endoscopes. For example, flexible upper endoscopy is often performed to evaluate for a gastrointestinal etiology of pain such as mucosal inflammation (esophagitis, gastritis, duodenitis), ulceration, or a neoplasm. Risks associated with flexible upper endoscopy include injury to the bowel wall, bleeding, and aspiration. Upper endoscopy is usually performed under conscious sedation, which carries risks as well. Furthermore, patients typically need to take a day off of normal activities due to the lasting effects of conscious sedation. Finally, the endoscopy procedure is clearly a cause of discomfort, pain and vomiting in many patients. Even the physical dimensions of the endoscope can be a cause for fear. Such risks, along with the prospect of incapacitation and fear, are often used as justifications by patients for delaying or altogether avoiding gastroscopic diagnosis.

Visualization of the GI tract, including the more difficult to reach areas, such as the small intestine, is possible today using an ingestible imaging device, for example a capsule. Images of the GI tract are obtained by a miniature image sensor carried by the device and are transmitted to an external recorder to be later viewed on a workstation. Sensing other parameters of the GI tract, such as pH or temperature, are also possible by using ingestible transmitting devices. Ingestible devices may be moved through the GI tract by the natural movement of peristalsis. However, in larger lumens, such as the stomach or large intestine, peristalsis alone may not be enough to move the capsule so that it covers the entire surface of the lumen wall.

SUMMARY OF THE INVENTION

There is thus provided, according to embodiments of the invention, a method for sensing a body lumen. According to some embodiments an ingestible sensing device, such as an imaging capsule (other suitable shapes or configurations may be used), is inserted into a body lumen. A subject (also referred to as patient) may be positioned in such a way so as to achieve corresponding positioning of the capsule within the patient's body lumen.

Controlled and repeatable positioning of a sensing device in vivo may be achieved according to embodiments of the present invention.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well known features may be omitted or simplified in order not to obscure the present invention.

According to an embodiment of the invention a sensing device is inserted in vivo and a patient is positioned in such a way so as to achieve corresponding positioning of the device within the patient's body lumen. Typically, a device used according to an embodiment of the present invention may be an autonomous compact device, which can be easily moved through a body lumen. Body lumens may include cylindrical tube like lumens, such as blood vessels or the small intestine, through which a device may be moved by the natural motion of the lumen, e.g., peristalsis in the small intestine. Other body lumens may be voluminous and not necessarily content filled, e.g., the stomach or large intestine. Movement through voluminous lumens may not be effected by natural muscle movement.

According to some embodiments a method is provided for moving a sensing device (e.g., an imaging device) through a subject's upper GI tract (which typically includes the esophagus and stomach).

According to one embodiment the device is an ingestible device, which may be, for example, a capsule (other suitable shapes or configurations may be used). An ingestible device may include an in vivo sensor, such as a pH sensor, a temperature sensor, a pressure sensor an image sensor and so on.

Typically, effective sensing of a lumen environment requires the sensor to be in the lumen for a minimal period of time and to survey most of the lumen volume.

According to an embodiment of the invention an imaging capsule shaped device may be used for sensing a patient's GI tract. The device may be, for example, similar to embodiments described in U.S. Pat. No. 5,604,531 to Iddan et al., and/or WO 01/65995, entitled "A Device And System For In Vivo Imaging", published on 13 Sep., 2001, both of which are assigned to the common assignee of the present invention and which are hereby incorporated by reference. However, the device may be any sort of in-vivo sensor device and may have other configurations. A device typically includes an image sensor, such as a CCD or CMOS imager, an illumination source, such as an LED and an optical system for focusing images onto the image sensor. The device may further include a transmitter for transmitting image and other (e.g., non-image) information to a receiving device, and may include other components, such as, for example, a compression module for compressing data. The transmitter is typically an ultra low power radio frequency (RF) transmitter with high bandwidth input, possibly provided in chip scale packaging. The transmitter may also include circuitry and functionality for controlling the device. The transmitter may be, for example, an ASIC, "computer on a chip", microcontroller, etc., or other component. Components such as the image sensor, illumination source and transmitter may be mounted on a support, which may be, for example, a printed circuit board or plastic board or sheet. The support may be another structure, and components need not be mounted on a separate support.

The device may be ingested for obtaining in vivo images or other in vivo information. Typically, the device is swallowed by a patient and traverses the patient's GI tract, however, other body lumens or cavities may be imaged or examined, and the device need not be swallowable. For example, a device may be inserted into the female reproductive tract or urinary tract for obtaining in vivo data. Typically, the device transmits information (e.g., image information) in discrete portions. Each portion typically corresponds to an image or frame. Other transmission methods are possible. For example, the device may capture image or other information once every half second, and, after capturing such an image, transmit the information to a receiving antenna. Other capture rates are possible. Typically, the image data recorded and transmitted is digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by, for example, a one byte (i.e., 0-255) brightness value. Other data formats may be used, and other image formats may be used.

Preferably, located outside the patient's body in one or more locations, are a receiver, preferably including an antenna or antenna array, for receiving image and possibly other data from the in vivo device, a receiver storage unit, for storing image and other data, a data processor, a data processor storage unit, and an image monitor, for displaying, inter alia, the images transmitted by the device and recorded by the receiver. Typically, the receiver and receiver storage unit are small and portable, and may be worn on the patient's body during recording of the images. Typically, the data processor, data processor storage unit and monitor are part of a personal computer or workstation, which may include standard components such as a processor, a memory (e.g., storage, or other memory), a disk drive, and input-output devices, although alternate configurations are possible. In alternate embodiments, the data reception and storage components may be of another configuration. It should be emphasized that other embodiments may include a wired rather than wireless device. According to some embodiments online viewing of a body lumen may be performed, wherein in vivo data is transmitted directly, typically through antennas surrounding a patient's body, to a receiving unit in a workstation. A receiving, processing, and display system may be, for example, as described in some embodiments of U.S. Pat. No. 5,604,531 to Iddan et al., and/or WO 01/65995, entitled "A Device And System For In Vivo Imaging", published on 13 Sep. 2001.

According to one embodiment, the imaging device may be spherical or substantially spherical (which when used herein includes an ellipse shape). Such a shape may enable the device to glide over the typically moist (and thus substantially frictionless) surface of body lumens, such as the stomach, when it is moved over the surface. Also, for example, a spherically shaped device may glide over the ridges formed on GI tract lumen walls (such as the stomach wall) rather than get stuck in these ridges. In such a case, the motion of an imager within the device may be relatively smooth and continuous. This may be in contrast to devices of other shapes (e.g., oblong shapes), which may produce jumpy motion and non-continuous images in the same context.

An optional ballast or weight may be added to a portion of an imaging (or other sensing) device. Ballast may allow one portion, such as the image sensor, to be usually oriented in a fixed direction. In alternate embodiments the internal components of a device may be packaged so as to shift the center of gravity [CG] and create ballast in one portion of the device, for example, batteries and electronic components may be packaged at one end of a capsule so as to create ballast at that end. In such an embodiment, the images captured tend to be not of the wall on which the device is resting, in the case that the device is resting on a surface in a lumen, but rather include a view oriented outward from the wall. In a lumen which is relatively voluminous (e.g., the stomach or large intestine), when the patient is oriented so gravity acts on the ballast or weight in a certain manner, the wall opposite the wall on which the device is resting is imaged, rather than a wall close to the device which may block the view of the imager. Such an embodiment may provide a relatively steady view of a lumen, and be easily oriented to portions of such lumens which are desired to be imaged. In alternate embodiments if sensing of a lumen wall is required, such as to sense a temperature or pH of a lumen wall tissue, where contact with the lumen wall may be preferable, ballast may be added to the sensing device so as to ensure positioning of the sensor in close vicinity of the lumen wall when the device is residing on the lumen wall. In yet further embodiments, a body lumen may be filled with a liquid to allow a sensing device to float or to be carried with the liquids to all parts of the lumen.

According to some embodiments an imaging device may be used which includes a plurality of image sensors. For example, a procedure according to an embodiment of the invention may include using an imaging capsule which includes two imagers positioned at the two ends of the capsule. Typically, such an imaging capsule may have a broader field of view than a capsule having one imager. Embodiments of imaging devices having a plurality of optical paths are described, for example, in WO02/054932, which was published on Jul. 18, 2002, and which is assigned to the common assignee of the present invention and which is hereby incorporated by reference.

Figure 1:
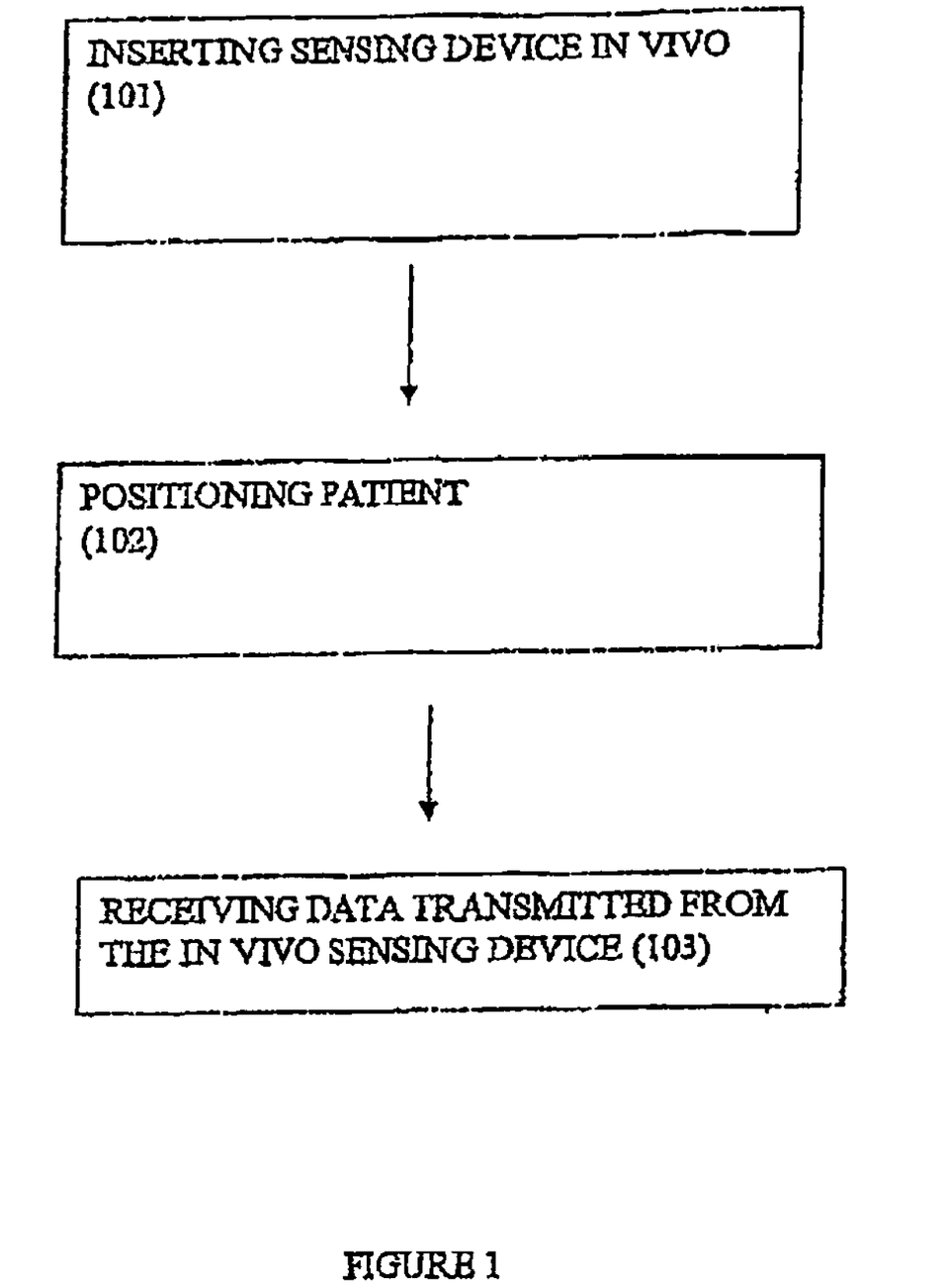
FIG. 1 is a box diagram depicting a method for in vivo sensing according to an embodiment of the invention.

Reference is now made to FIG. 1, which schematically shows a method according to an embodiment of the invention. An in vivo sensing device, for example, a device as described above, is inserted in vivo (101), typically in to a patient's body lumen. The patient is positioned (102) typically to achieve a desired positioning of the in vivo sensing device in the patient's body and/or to control the timing of the in vivo sensing process.

According to one embodiment the in vivo sensing device is inserted in vivo by swallowing. According to other embodiments a device may be inserted in vivo by using instruments such as endoscopes, needles, etc. Other inserting methods are possible according to additional embodiments of the invention. The patient may be positioned prior to the insertion of the sensing device or the positioning may commence after the device is inserted into the patient's body. According to one embodiment positioning may include rotating or tilting a patient's body or parts of a patient's body. According to other embodiments positioning may include moving a patient's body or parts of a patient's body in a specific direction and/or at a specific rate and/or at predetermined intervals etc. it should be appreciated that the sequence of positioning of the patient's body may directly affect the path taken by the device in vivo and accordingly may affect the coverage of the body lumen. A patient's body may be prepped prior to insertion of the sensing device or at other points during the procedure. For example, a patient's lumen may be emptied (such as by performing an enema for the large intestine) or filled (such as by drinking a large volume of liquid), specific active ingredients may be ingested, for example, to achieve relaxation of muscles, (e.g., to alter peristalsis or to achieve vasodilation of blood vessels) or for example, saliva reducing agents may be ingested such as, water, glycerin, oil or other suitable saliva reducing agents. The method according to an embodiment of the invention may include the step of receiving data transmitted from the in vivo sensing device (103). According to one embodiment in vivo data is transmitted from the device to a recorder worn by the patient and is later down loaded to a workstation for reviewing off line. According to yet another embodiment in vivo data may be transmitted directly to a workstation for online review. According to one embodiment the sequence of patient positioning may be dependant on online data review. For example, a patient may be positioned such that a first portion of his stomach may be viewed. If data obtained from the first portion shows the occurrence of a pathology in this portion the patient is not positioned according to the predetermined positioning sequence but rather he is delayed in the first position or alternatively, a different positioning sequence is applied in order to obtain more data from the first portion of the patient's stomach.

According to one embodiment there is provided a method for sensing a patient's esophagus. According to an embodiment of the invention an imaging capsule, such as an imaging device having two imagers positioned at the two ends of the capsule e.g. M2A™ imaging capsule, is inserted into a patient's esophagus and the patient is positioned such that, inter alia, the capsule stays in the esophagus for a minimal period that may be required to obtain significant data and to achieve a survey of most of the esophagus. A method for imaging the esophagus is exemplified by the following representative procedures. It will be appreciated that a person skilled in the art may adjust the procedures according to specific requirements or patient physique.

EXAMPLES

Example 1

Procedure I for Esophagus Capsule Endoscopy

Figure 2:
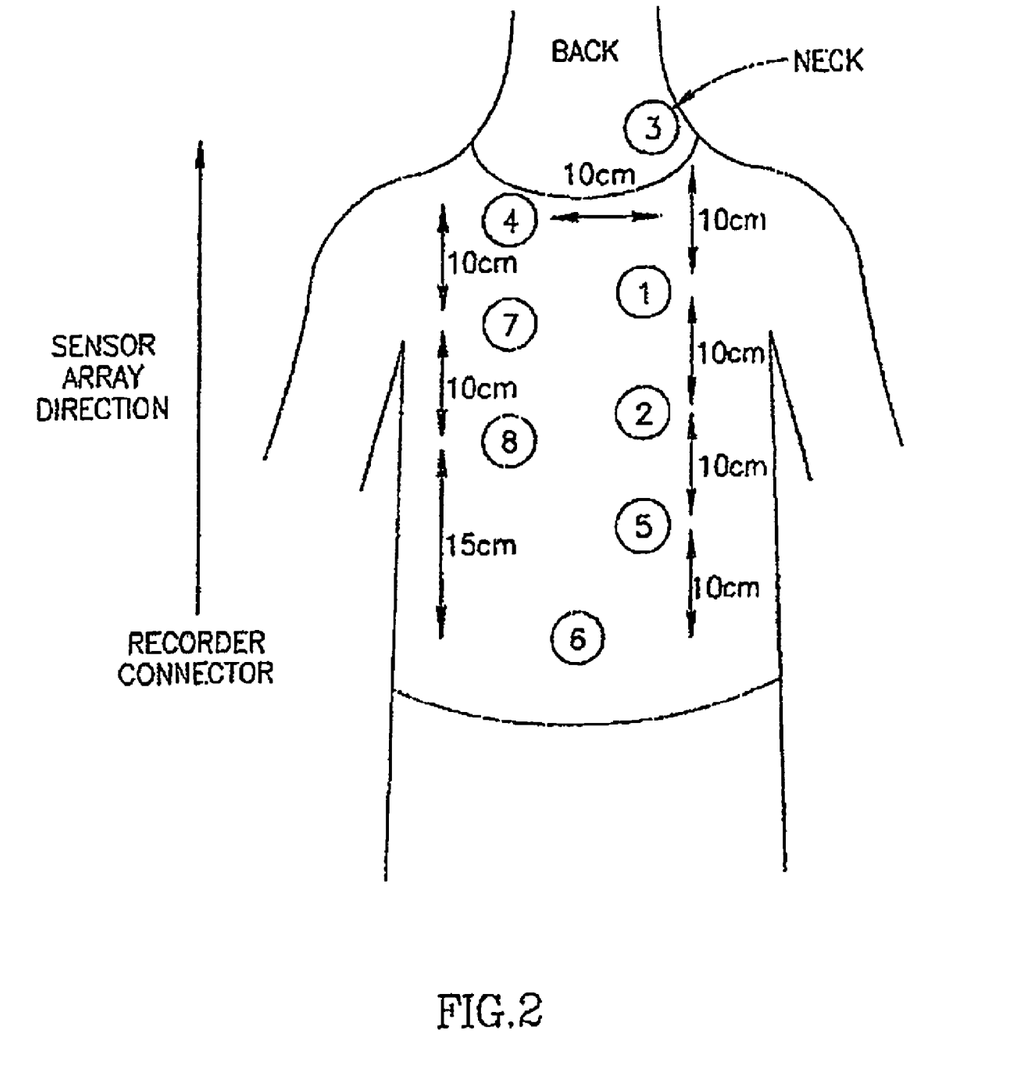
FIG. 2 is a schematic presentation of a receiving unit placed on a patient's body during a procedure in accordance with an embodiment of the invention.

1. Placement of sensors (e.g. antennas) on a patient's back (see FIG. 2—measurements are shown from center to center of sensors. Measurements can be varied according to patient's physique), after which the patient may lie on his back.
2. Attachment of sensor array to recorder.
3. Rinsing saliva—in order to minimize the amount of saliva in the esophagus:
   א. Patient is positioned lying down or so that he may immediately lie down to a horizontal position.
   ב. About 250 cc of water are sipped by the patient in a series of small sips. The last sip is used to swallow an M2A™ imaging capsule (glycerin or oil (e.g., 3-5 ml) may be also used to minimize amount of saliva).
   ג. During this process the patient may not speak.
4. Ingestion of imaging capsule:
   א. When swallowing the capsule patient should take care to have the imaging side of the capsule pointing down into the pharynx.
   ב. Patient should assume a horizontal position and swallow capsule (optionally—swallowing with head slightly raised and laying down immediately after swallowing).
   ג. Patient should keep his mouth open for, for example, approximately 3 minutes after swallowing.
5. Start positive inclination by raising torso in a stepwise manner of 20-30 degrees every minute.
6. When reaching sitting position wait 1 minute before allowing patient to stand up.

Example 2

Procedure II for Esophagus Capsule Endoscopy

1. Training a patient to drink sips of 115 ml of water through a straw. For example, while lying in a right lateral position, e.g. in a right lateral decubitus position, a patient is trained to drink water through a straw from a Training Cup, e.g. a ~300 ml cup with cover, hole for straw, and flexible straw, filled with 120 ml of room temperature drinking water. The patient may be positioned on his right side with his head on a pillow. The patient is asked to drink 4-8 sips of water using the straw without moving or raising his head. The volume of the sips is observed and the patient is asked to increase or decrease the volume until the sip volume was approximately 15 ml. Confirmation that the subject felt comfortable with the ingestion procedure is obtained.
2. No head or body movement and no talking are allowed until the end of the procedure;
3. The patient ingests water e.g. 100 ml, to clear saliva;
4. Positioning the patient in a right lateral position e.g. a right lateral decubitus position;
5. Inserting a sensing device into the patient's body lumen while the patient is lying flat on his right side. For example, while lying flat on his right side, e.g. a right lateral decubitus position, the patient swallows an imaging device with a single sip of water, e.g. ~15 ml, and stay in right side position. According to some embodiments of the present invention, the patient may be positioned lying in a right lateral decubitus position with his head on a pillow. The Ingestion Cup, e.g. filled with 300 ml of room temperature drinking water, may be placed on the patient's bed, for example close to the patient's mouth. If the subject could not ingest the capsule in the flat position, the head of the bed is elevated by up to 2.5 inches;

6. Administering one sip of water every 30 sec for 7 minutes to the subject. For example, after ingestion of the imaging device and while remaining lying on his right side, the patient is asked to drink additional sips of water for 7 minutes, one sip, e.g. ~15 ml, every ~30 seconds; and 7. Positioning the patient in an upright sitting position and administering an additional sip of water to the subject. For example, at 7 minutes post ingestion, the patient is asked to sit upright and drink an additional sip of water; and 8. The patient is allowed to get up and walk for the next 15 minutes. No food or drink is allowed during this time.

As with all examples provided herein, other suitable periods of time or ranges may be used. According to one embodiment the sensors are connected directly to the workstation and the procedure is carried out with online viewing of the patient's esophagus.

According to another embodiment there is provided a method for sensing a patient's stomach. According to an embodiment of the invention an imaging capsule, such as an M2A™ imaging capsule, is inserted into a patient's stomach and the patient is positioned such that, inter alia, the capsule senses the stomach body, including remote areas such as the cardia, fundun, antrum and the pyloric canal. A method for imaging the stomach is exemplified by the following representative procedures and experiments. According to some embodiments, in the following exemplary procedures patients were instructed to move smoothly from position to position and roll gently once reaching each position. It will be appreciated that a person skilled in the art may adjust the procedure according to specific requirements or patient physique.

Example 2

Procedure I for Stomach Capsule Endoscopy

1. While lying flat on his left side, the patient swallows an M2A™ imaging capsule with 50 ml of water;
2. The patient is positioned Back Trendelenburg −10 to −20 degrees for about 1 minute;
3. The patient is positioned on his left side with his head elevated at 45 degrees for about 1 minute;
4. The patient is positioned on his left side with his head elevated at 60 degrees for about 1 minute;
5. The patient is positioned on his left side with his head elevated at 80 degrees for about 1 minute;
6. The patient is positioned flat on his back for about 1 minute;
7. The patient is positioned flat on his left side for about 1 minute;
8. The patient is positioned flat on his back again for about 1 minute; The patient is positioned flat on his abdomen for about 1 minute; The patient is positioned flat on his right side for about 1 minute.

Example 3

Procedure II for Stomach Capsule Endoscopy

1. The patient ingests 200-300 ml water. After 45-60 minutes the patient swallows an imaging capsule having two imagers positioned at the two ends of the capsule, with 20-30 ml of water;
2. The patient is laid on his back (0°) for 1 minute;
3. The patient is positioned on his left side (0°) for 1 minute;
4. The patient is positioned on his back (0°) for 1 minute;
5. The patient is positioned on his left side (0°) for 1 minute;
6. The patient is positioned on his back (0°) for 1 minute;
7. The patient is positioned on his left side (30°) for 1 minute;
8. The patient is positioned on his left side (60°) for 1 minute;
9. The patient is positioned sitting upright with legs dangling (90°) for 1 minute;
10. The patient is positioned on his back (0°) for 1 minute;
11. The patient is positioned on his left side (0°) for 1 minute;
12. Optional—patient ingests about 300 ml of water;
13. The patient is positioned on his back (0°) for 1 minute;
14. The patient is positioned on his abdomen (0°) for 1 minute;
15. Through his right hand side the patient is positioned on his right side (0°) for 15 minutes.

An experiment was carried out to test the above positioning procedures. According to one embodiment the capsule images are viewed on-line throughout the procedure, which lasts approximately 30 minutes. The subject is directed through the positioning set, and a fluoroscopic image of the stomach is captured in each position. At completion of the positioning set the subject is released. It was anticipated that each change in position of the patient would move the capsule along a predictable path to a particular region of the stomach.

RESULTS

Nine trials were conducted using the above procedures, with some variation, especially in the early trials. In all the trials, the capsule reached every region of the stomach at least once, except the pylorus. In two trials, the capsule also reached the pylorus, in one case after 23 minutes and in the other case after 31 minutes. Trial duration varied from 22 to 37 minutes. Image quality was good in most cases. The patient ingests 50 ml of contrast medium in water. Some results are summarized in table no. 1.

TABLE NO. 1

| Required EndPoint | Position Set | Anticipated Path Capsule | Validated by Spot Fluoroscopy Subject ID | | | | | | | | |
|---|---|---|---|---|---|---|---|---|---|---|---|
| | | | 200 | 201 | 202 | 203 | 204 | 206 | 207 | 208 | 209 |
| FUNDUS | Back Flat | Fundus | Y | Y | Y | Y | Y | Y | Y | Y | Y |
| | Left Flat | Fundus or Body | Y | Y | Y | Y | Y | Y | Y | Y | Y |
| | Back Minus 10 degrees | Fundus | Y | Y | Y | Y | Y | Y | Y | Y | Y |
| ANTRUM | Left 45 degrees | Fundus or Body | Y | Y | Y | Y | Y | Y | Y | Y | Y |
| | Left 60 degrees | Body | | Y | Y | Y | N | Y | Y | Y | N |
| | Left 80 degrees | Antrum | Y | Y | Y | Y | Y | Y DELAY | Y | Y | Y |
| FUNDUS | Back Flat | Fundus or Antrum | Y | Y | Y | Y | Y | Y | N | Y | Y |
| | Left Flat | Body | | | Y | Y | Y | N | Y | Y | Y |
| | Back Flat | Fundus | Y | N | Y | Y | Y | Y | Y | Y | Y |
| PYLORUS | Abdomen Flat | Pylorus or Antrum | Y | N | Y | Y | N | Y | N | N | Y |
| | Right Flat | Pylorus | N | N | N | N | N | N | N | N | N |
| | | Pylorus as per video | N | N | Y | N | N | N | N | Y | N |
| | | Pylorus Arrival Time | | 0:31:13 | | | | | | 0:23:33 | |
| | | Recording Time | 0:24:34 | 0:26:43 | 0:37:09 | 0:26:59 | 0:22:33 | 0:22:53 | 0:24:05 | 0:23:59 | 0:24:24 |

CONCLUSIONS

1. The positioning set is successful in moving the capsule in a predictable manner to all areas of the stomach, except the pyloric region.
   In only 2 cases out of 9, the capsule reached the pylorus within the 30-minute trial time.
3. The capsule did not pass into the duodenum within the 30-minute trial time in any of the trials.
4. Sensor placement: It was concluded in an investigation of the results that no gaps occurred due to low level sensor signals. It is possible that a single sensor would be sufficient for gastric screening.

According to some embodiments of the present invention, there is provided a procedure for sensing a patient's body lumen, e.g. the stomach or the esophagus, in real time. The in-vivo sensing system may include a workstation and/or a portable device, capable of downloading images from the receiver and capable of processing and/or analyzing and/or displaying images in real time. The portable device may include a display unit, and may be able to display the images on the display unit. For example, the receiver may be able to transfer a received and/or recorded information to a portable device, such as a SONY VAIO™ lightweight belt-portable computer, a personal digital assistant, and/or to the work station via, for example, a wireless or hard-wired medium such as a USB cable, and may be able to do so while receiving/recording information from the sensing device and while the sensing device is inside a patient's body. According to one embodiment of the present invention, during a Procedure for Esophagus Capsule Endoscopy or a Procedure for Stomach Capsule Endoscopy the patient or the physician may see in real time, for example on the display, when the sensing device enters a body lumen, for example the stomach, and may shorten the procedure time for example to less than 2 minutes.

According to some embodiments of the present invention, the real time procedure may improve pathology or anatomy visualization by controlling the movement and positioning of the capsule in various sites in the GI tract such as the esophagus and stomach. For example, a physician and/or the patient may see in real time, for example on the display, when the sensing device visualizes pathology and may avoid water sips during this time, e.g. to allow extended sensing device 'parking' in proximity to the pathology. Another example, a physician and/or the patient may see in real time, for example on the display, some portion of the stomach or stomach pathology and may change patient positioning to move the capsule to different location in the stomach and thus providing additional information on same or other parts of the stomach.

Figure 3:
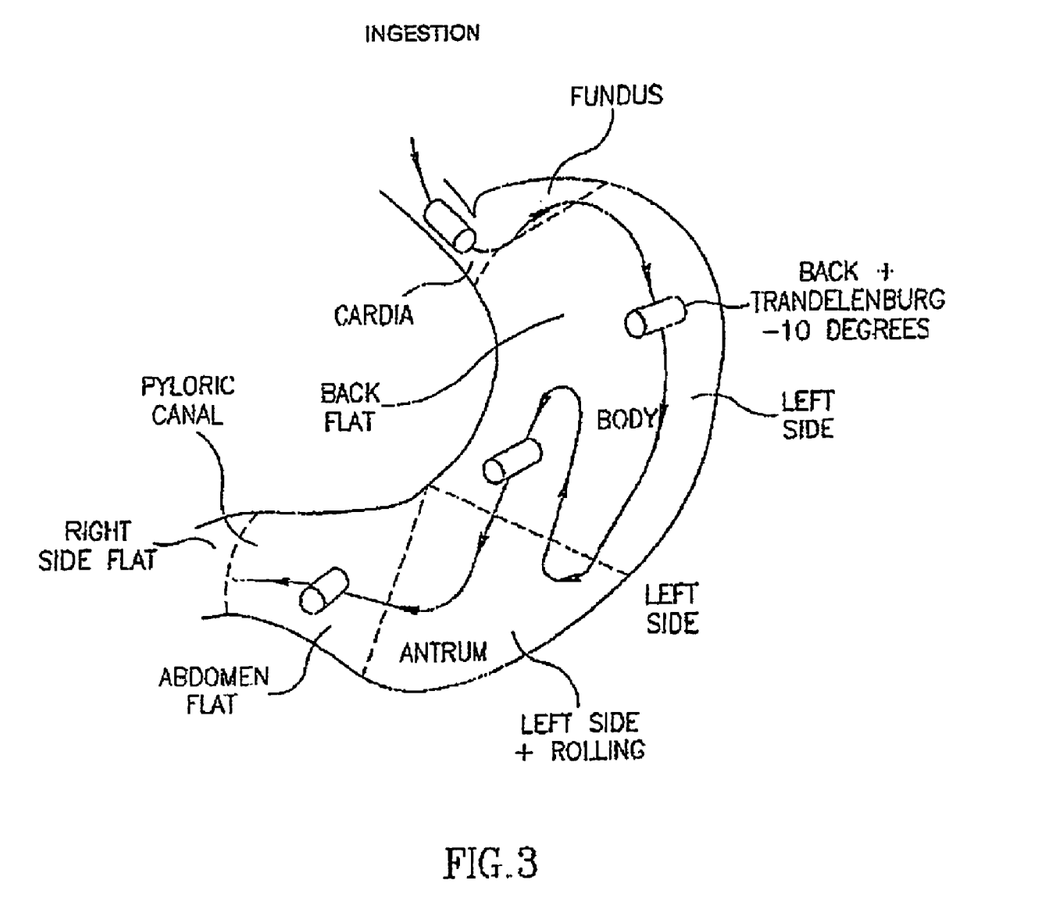
FIG. 3 is a schematic illustration of a device that is moved about a patient's stomach according to an embodiment of the invention.

FIG. 3 schematically illustrates a swallowable capsule that is moved about a patient's stomach according to the above Procedure for Stomach Capsule Endoscopy. It can be seen that the capsule follows a track that covers most of the stomach body, including remote areas such as the cardia, fundum, antrum and the pyloric canal.

Thus, a method according to embodiments of the invention may provide a means for predictably and controllably moving a device in a body lumen. By the method according to embodiments of the invention a required area in a body lumen may be covered at a desired time schedule, thereby providing an effective and controllable tool for diagnosing and/or screening body lumens.

It will be appreciated by persons skilled in the art that the present invention is not limited by what has been particularly shown and described herein above. Rather the scope of the invention is defined by the claims, which follow.

We claim:
1. A method for in vivo sensing of an esophagus, the method comprising:
   inserting an autonomous sensing device into a subject's esophagus while the subject is lying flat in a horizontal position on his right side;
   administering one sip of water every 30 sec for 7 minutes to the subject;
   positioning the subject in an upright sitting position;
   administering an additional sip of water to the subject;
   sensing data as the sensing device moves through the esophagus; and
   receiving data transmitted from the sensing device.
2. The method according to claim 1 wherein sensing comprises imaging the subject's esophagus.
3. The method according to claim 1 comprising ingesting a saliva reducing agent prior to inserting a sensing device into a subject's body lumen.

4. The method according to claim 3 wherein the step of ingesting a saliva reducing agent comprises ingesting a saliva reducing agent including glycerin.

5. The method according to claim 3 wherein the step of ingesting a saliva reducing agent comprises ingesting a saliva reducing agent including oil.

6. The method according to claim 1 comprising training a patient to drink sips of ~15 ml of water through a straw.

7. The method according to claim 1 comprising substantially emptying the subject's esophagus prior to inserting a sensing device into a subject's body lumen.

8. The method according to claim 1 comprising receiving data transmitted from the sensing device in real time.

* * * * *

UNITED STATES PATENT AND TRADEMARK OFFICE
CERTIFICATE OF CORRECTION

PATENT NO. : 7,628,753 B2
APPLICATION NO. : 11/452404
DATED : December 8, 2009
INVENTOR(S) : Rabinovitz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 445 days.

Signed and Sealed this

Twenty-first Day of December, 2010

David J. Kappos
*Director of the United States Patent and Trademark Office*